United States Patent [19]

Ishikawa et al.

[11] Patent Number: 4,614,742

[45] Date of Patent: Sep. 30, 1986

[54] FLUORINATED ISOPHTHALONITRILE COMPOUND AND NONMEDICAL FUNGICIDE CONTAINING THE SAME

[75] Inventors: Nobuo Ishikawa, Yokohama; Akio Takaoka, Kawasaki; Takashi Isono, Tokyo; Masatoshi Motoyoshi, Tokyo; Kazuhiro Kojima, Tokyo, all of Japan

[73] Assignee: S.D.S. Biotech K.K., Tokyo, Japan

[21] Appl. No.: 770,481

[22] Filed: Aug. 29, 1985

[51] Int. Cl.[4] ............ A01N 43/84; A01N 37/34; C07C 121/78

[52] U.S. Cl. .................. 514/237; 514/269; 514/274; 514/329; 514/331; 514/383; 514/394; 514/395; 514/398; 514/399; 514/406; 514/407; 514/471; 514/524; 514/525; 544/163; 544/311; 544/316; 544/317; 546/223; 546/230; 548/262; 548/266; 548/269; 548/329; 548/330; 548/337; 548/341; 548/375; 548/378; 549/495; 558/419

[58] Field of Search .............. 558/419; 549/495; 548/262, 266, 269, 329, 330, 337, 341, 375, 378; 546/223, 230; 544/163, 311, 316, 317; 514/237, 269, 274, 329, 331, 383, 394, 395, 398, 399, 406, 407, 471, 524, 525

[56] References Cited

U.S. PATENT DOCUMENTS 3,290,353 12/1966 Battershell et al. .............. 558/419
3,637,796 1/1972 Battershell ..................... 558/419
4,069,342 1/1978 Magee .......................... 514/525
4,263,206 4/1981 Anderson ....................... 260/195

*Primary Examiner*—Dolph H. Torrence
*Attorney, Agent, or Firm*—Sughrue, Mion, Zinn, Macpeak and Seas

[57] ABSTRACT

A fluorinated isophthalonitrile compound having the general formula

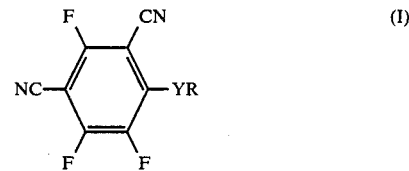

wherein Y is —O, —S, or —N(R'), R and R' are independently hydrogen, an alkyl group, an alkyl group, an alkynyl group, a haloalkyl group, an alkoxyl group, alkoxyalkyl group, a phenyl group which may be substituted, a tetrahydrofurfuryl group, or a cycloalkyl group, provided that, in the case of Y=—N(R'), R and R' or Y may be a tetrahydrofurfuryl group, or a cycloalkyl group, a heterocyclic compound residue.

This fluorinated isophthalonitrile compound is suitable for use as an agricultural fungicide.

4 Claims, No Drawings

FLUORINATED ISOPHTHALONITRILE COMPOUND AND NONMEDICAL FUNGICIDE CONTAINING THE SAME

BACKGROUND OF THE INVENTION

1. Field of the Invention

The present invention relates to a novel fluorinated isophthalonitrile compound suitable for use as an agricultural fungicide or germicide as well as antibacterial and mildewproofing agent for various industrial products and the raw materials thereof. The present invention also relates to a nonmedical fungicide.

2. Description of the Related Art

It is heretofore known, as shown in, for example, Japanese Examined Patent Publication (Kokoku) No. 41-11358, that halogenated aromatic dinitriles have biological activities suitable for use as a fungicide, a bactericide, a nematocide, and a herbicide. 4-Alkoxy-2,5,6-trichloroisophthalonitrile compounds are also known as a mildewproofing agent as shown in, for example, Japanese Unexamined Patent Publication (Kokai) No. 50-121424. Furthermore, it has recently become problems that various industrial products and the raw materials thereof are damaged by microorganisms such as bacteria, fungi, and yeasts. These damages not only detract from the external appearance and health and sanitary properties, but also detrimentally affect performance and qualities. In order to prevent these damages, it is strongly desired in the art to develop antibacterial and mildewproofing agent having large antibacterial and mildewproofing effects, wide antibacterial spectra, and other properties depending upon the usage thereof (e.g., water resistance, heat resistance, light resistance, decomposability, and stability).

SUMMARY OF THE INVENTION

Accordingly, the objects of the present invention are to provide novel compounds having the above-mentioned desired antibacterial and mildewproofing effects and having excellent agricultural fungicidal properties.

Other objects and advantages of the present invention will be apparent from the following description.

In accordance with the present invention, there is provided a fluorinated isophthalonitrile compound having the general formula

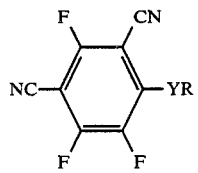

wherein Y is —O—, —S—, or —N(R'), R and R' and independently hydrogen, an alkyl group, preferably having 1 to 10 carbon atoms, an alkenyl group, preferably having 3 to 10 carbon atoms, an alkynyl group, preferably having 3 to 10 carbon atoms a haloalkyl group preferably having 1 to 10 carbon atoms, an alkoxyl group, preferably having 1 to 10 carbon atoms, an alkoxyalkyl group, preferably having 2 to 10 carbon atoms, a phenyl group which may be substituted, a tetrahydrofurfuryl group, or a cycloalkyl group, preferably having 3 to 8 carbon atoms, provided that, in the case of Y=—N(R'), R and R' or Y may be a heterocyclic compound residue, preferably pyrazol-3-yl, 1,2,4-triazol-3-yl, benzimidazol-2-yl, 2(1H)-pyrimidinon-6-yl, imidazol-1-yl, pyrazol-1-yl, pyrimidine-2,4(1H,3H)-dion-1-yl, morpholino, piperidino group which may be substituted.

In accordance with the present invention, there is also provided a nonmedical fungicide comprising, as an effective ingredient, the fluorinated isophthalonitrile having the above-mentioned general formula (I).

DESCRIPTION OF THE PREFERRED EMBODIMENTS

According to the present invention, there is provided novel fluorinated isophthalonitrile compounds having the above-mentioned general formula (I). Typical examples of such compounds are shown in Table 1.

TABLE 1

| Compound No. | —YR in formula (I) | Physical Property: Melting point (mp), Boiling point (bp), Refractive index ($n_D$) |
|---|---|---|
| 1 | —NH$_2$ | mp 191–193° C. |
| 2 | —NHCH$_3$ | mp 107–109° C. |
| 3 | —NHC$_2$H$_5$ | mp 75–77° C. |
| 4 | —NHC$_4$H$_{9-n}$ | bp 165–167° C./2.5 mmHg |
| 5 | —N(C$_4$H$_{9-n}$)$_2$ | bp 137–139° C./2.5 mmHg |
| 6 | —NH—C$_6$H$_5$ | mp 131.5–134° C. |
| 7 | —NH—C$_6$H$_4$—Cl | mp 167° C. |
| 8 | —NH—C$_6$H$_3$Cl$_2$ | mp 158° C. |
| 9 | —NH-(1,2,4-triazol-3-yl) | mp 260° C. |
| 10 | —NH-(benzimidazol-2-yl) | mp 260° C. or more |
| 11 | —N-(imidazol-1-yl) | mp 260° C. or more |
| 12 | —N-piperidino | mp 64–66° C. |
| 13 | —NH-(pyrimidine-2,4(1H,3H)-dion-1-yl) | mp 190–191° C. |

TABLE 1-continued

| Compound No. | —YR in formula (I) | Physical Property: Melting point (mp), Boiling point (bp), Refractive index ($n_D$) |
|---|---|---|
| 14 | —N(C$_2$H$_5$)$_2$ | bp 144–146° C./7 mmHg |
| 15 | 1,2,4-triazol-1-yl (–N connected to N=CH–N=CH ring) | mp 209–210° C. |
| 16 | 5-fluorouracil-1-yl (–N in uracil with F at 5-position) | mp 260° C. or more |
| 17 | morpholino (–N(CH$_2$CH$_2$)$_2$O) | mp 211° C. |
| 18 | 2,6-dimethylmorpholino | mp 138–139° C. |
| 19 | —OH | mp 168–172° C. |
| 20 | —OCH$_3$ | mp 71–72° C. |
| 21 | —OC$_2$H$_5$ | mp 59–62° C. |
| 22 | —SC$_2$H$_5$ | $n_D^{18.5}$ 1.5610; bp 115–118° C./0.3 mmHg |
| 23 | —O—n-C$_3$H$_2$ | mp 54–56° C. |
| 24 | —O—i-C$_3$H$_7$ | mp 63–64° C. |
| 25 | —O—n-C$_4$H$_9$ | bp 134–136° C./0.3 mmHg |
| 26 | —O—i-C$_4$H$_8$ | bp 121–123° C./0.3 mmHg |
| 27 | OCH$_2$CH=CH$_2$ | mp 50° C. or less, $n_D^{30}$ 1.5136 |
| 28 | —OCF$_3$CH$_2$ | $n_D^{27}$ 1.4635 |
| 29 | —O—phenyl | mp 81–85° C. |
| 30 | —O—(2-methylphenyl) | mp 119–121° C. |
| 31 | —O—(3-methylphenyl) | mp 55° C. or less |
| 32 | —O—(4-methylphenyl) | mp 99–101° C. |
| 33 | —O—(2-chlorophenyl) | mp 96–98° C. |
| 34 | —O—(4-chlorophenyl) | $n_D^{26}$ 1.5608 |
| 35 | —O—(2,4-dichlorophenyl) | mp 55° C. or less |
| 36 | —O—(3,4-dimethylphenyl) | mp 88–91° C. |
| 37 | —O—(2,6-dimethylphenyl) | mp 110–115° C. |
| 38 | —O—(4-fluorophenyl) | mp 55° C. or less |
| 39 | —O—(2-chloro-4-methylphenyl) | mp 84° C. |
| 40 | —O—(4-nitrophenyl) | mp 90–95° C. |
| 41 | —S—phenyl | mp 90–92° C.; bp 65–67° C./0.7 mmHg |
| 42 | —O—CH$_2$C(CH$_3$)=CH$_2$ | mp 50° C. or less |
| 43 | —O—CH$_2$CH$_2$OCH$_3$ | $n_D^{24}$ 1.5030 |
| 44 | —O—CH$_2$–(tetrahydrofuran-2-yl) | $n_D^{24}$ 1.5186 |
| 45 | —O—n-C$_6$H$_{13}$ | $n_D^{24}$ 1.4937 |
| 46 | —O—n-C$_8$H$_{17}$ | $n_D^{24}$ 1.4906 |

TABLE 1-continued

| Compound No. | —YR in formula (I) | Physical Property Melting point (mp), Boiling point (bp), Refractive index ($n_D$) |
|---|---|---|
| 47 | —O—⟨C₆H₅⟩ (H) | $n_D^{24}$ 1.5036 |
| 48 | —O—CH(CH₂CH₃)(CH₃) | bp 113° C./0.21 mmHg |
| 49 | —S—CH₃ | mp 50° C. or less, $n_D^{40}$ 1.5651 |
| 50 | —S—n-C₃H₇ | mp 50° C. or less, $n_D^{40}$ 1.5524 |
| 51 | —S—iso-C₃H₇ | mp 50° C. or less, $n_D^{40}$ 1.5495 |
| 52 | —S—n-C₄H₉ | bp 138–139° C./0.3 mmHg, $n_D^{28}$ 1.5486 |
| 53 | —S—iso-C₄H₉ | bp 120–121° C./0.18 mmHg, $n_D^{28}$ 1.5403 |
| 54 | —S—sec-C₄H₉ | bp 106–108° C./0.15 mmHg, $n_D^{40}$ 1.5440 |

The fluorinated isophthalonitrile compounds having the general formula (I) according to the present invention can be prepared as follows.

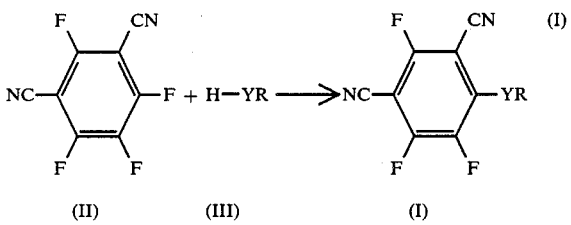

wherein Y and R are the same as defined above.

Thus, the starting materials (II) and (III) are mixed to allow to be reacted in the presence or absence of a solvent to form the desired fluorinated isophthalonitrile compounds (I). The reaction is preferably carried out at a temperature between −20° C. and the reflux temperature of a solvent. The starting material (III) may be used as a reaction solvent. Alternatively, aprotic solvents such as acetonitrile, chloroform, dichloromethane, benzene, toluene, dioxane, ethyl ether, tetrahydrofuran, and ethyl acetate may be used as a reaction solvent. Furthermore, the above-mentioned reaction can be advantageously accelerated when a catalytic amount, or an amount equimolecular to 10 times the starting material (II), of a base such as an alkali hydroxide, triethylamine, pyridine, an alkali carbonate, or potassium fluoride is used.

The starting compound (II), i.e., tetrafluoroisophthalonitrile, can be prepared from tetrachloroisophthalonitrile in a known manner (see, for example, British Pat. No. 1026290 (1966), Bull. Chem. Soc. Japan 40, 688 (1966), Kagaku Kogyo Zasshi (Japan) 73, 447 (1970), and Japanese Examined Patent Publication No. 41-11358).

The fluorinated isophthalonitrile compounds according to the present invention have excellent and remarkable mildewproofing action and antibacterial action and also have wide action spectra and are very stable against ultraviolet light. Furthermore, when the fluorinated isophthalonitrile compounds according to the present invention are used as an agricultural fungicide in the field or as an industrial antibacterial and mildewproofing agent outdoors, the compounds exhibit excellent prolonged activity.

The nonmedical fungicides according to the present invention contain, as an effective or active ingredient, one or more of the above-mentioned fluorinated isophthalonitrile compounds, preferably in an amount of 1% to 95% by weight, more preferably 10% to 80% by weight, of the total amount of the composition. Thus, the present fungicide has excellent curative effects (i.e., effects obtained by directly applying the present agent to the portion where harmful fungi or bacteria are generated) and excellent preventive effects (i.e., effects obtained by applying the present agent to the portion where harmful fungi or bacteria are expected to be generated).

The above-mentioned effective compounds according to the present invention can be directly used as a nonmedical fungicide. Furthermore, the present compounds can be formulated with bases to form various forms of preparations such as powder, wettable powder, tablets, oily agents, gaseous agents, emulsions, aerosols, and fumigants.

These bases usable in the formulation of the present fungicides may be in the form of solid, liquid, or gas. Examples of the solid bases usable in the present invention are talc, clay, kaolin, diatomaceous earth, calcium carbonate, potassium chlorate, silica, niter, woodmeal, nitrocellulose, starch, wheat flour, soybean flour, and gum arabic.

Examples of the liquid bases usable in the present invention are water and organic solvents. Typical examples of the organic solvents are hydrocarbons such as benzene, toluene, xylene, kerosine, diesel oil, fuel oil, petroleum, and naphtha; ketones such as acetone, methylethyl ketone, and cyclohexanone; chlorinated hydrocarbons such as carbon tetrachloride, chloroform, trichloroethylene, and perchloroethylene; amyl acetate and butyl acetate; monoalkyl ethers, e.g., monomethyl ether and monoethyl ether, of ethylene glycol; and alcohols such as methanol, ethanol, isopropanol, and amyl alcohol.

Examples of the gaseous bases usable in the present invention are air, nitrogen, carbon dioxide, Freon (registered trademark of DuPont for fluorohydrocarbons), propane, and butane.

In addition to the above-mentioned bases, various conventional ingredients can be optionally incorporated into the present germicide. For example, nonionic, anionic, cationic, or ampholytic surfactants can be used as an adjuvant (i.e., a wetting agent, emulsifier, dispersing agent, spreader).

The nonmedical germicides according to the present invention are effective for controlling a wide variety of diseases of various agricultural and garden crops and are also effective against microorganisms, such as fungi, algae, bacteria, and organisms of slime, which adversely affect industrial products or the starting materials thereof. Examples of such diseases and microorganisms are as follows.

| Crops | Group I (Diseases) Diseases |
|---|---|
| Rice | Blast |
|  | Brown spot |

-continued

| Group I (Diseases) | |
|---|---|
| Crops | Diseases |
| Wheat | Sheath blight |
| | Bacterial leaf blight |
| | Spot blotch |
| | Snow mold |
| | Typhula snow blight |
| Potato | Late blight |
| | Early blight |
| | Black scurf |
| Pulse | Brown spot |
| | Frog-eye leaf spot |
| | Downy mildew |
| | Stem rot |
| Tobacco | Wild fire |
| | Black shank |
| Tea | Bacterial shoot blight |
| | Blister blight |
| | Net blister blight |
| | Anthracnose |
| | Gray blight |
| Sugar beet | Downy mildew |
| | Cercospora leaf spot |
| | Damping-off |
| Tomato | Bacterial canker |
| | Late blight |
| | Gray mold |
| | leaf mold |
| | Fusarium wilt |
| | Stem rot |
| | Damping-off |
| | Early blight |
| Cucumber | Gray mold |
| | Downy mildew |
| | Phytophthora rot |
| | Scab |
| | Damping-off |
| | Anthracnose |
| | Gummy stem blight |
| | Fusarium wilt |
| Japanese raddish (daikon) | Black rot |
| | Bacterial soft rot |
| | Yellows (wilt) |
| | Gray leaf spot |
| | (Alternaria leaf spot) |
| | Downy mildew |
| Onion | Bacterial soft rot |
| | Downy mildew |
| | Gray-mold neck rot |
| Lettuce | Bacterial soft rot |
| | Stem rot |
| Citrus fruit | Gray mold |
| | Canker |
| | Melanose |
| | Scab |
| Apple | Blossom blight |
| | Scab |
| | Alternaria leaf spot |
| Japanese persimmon (kaki) | Gray mold |
| | Circular leaf spot |
| | Angular leaf spot |
| | Anthracnose |
| Japanese pear | Scab |
| | Black spot |
| Peach | Brown rot |
| | Scab |
| | Phomopsis rot |
| | Bacterial shot hole |
| Grape | Downy mildew |
| | Anthracnose |
| | Gray mold |
| | Ripe rot |

Group II (Microorganisms which adversely affect industrial products and the raw materials thereof)

Bacillus spp., Staphylococcus spp.,
Escherichia spp., Pseudomonas spp.,
Serratia spp., Alternaria spp.,
Aspergillus spp., Penicillium spp.,
Cladosporium spp., Mucor spp.,
Rhizopus spp., Gliocladium spp.,
Eurotium spp., Aureobasidium spp.,
Chaetomium spp., Fusarium spp.,
Myrothecium spp., Rhodotorula spp., and
Saccharomyces spp.

The nonmedical fungicide according to the present invention can be preferably used in a concentration of 1 to 1000 ppm, more preferably 10 to 500 ppm, in the formulated composition, although the concentration of the active component depends upon the kinds of diseases and microorganisms. Thus, the above-mentioned diseases can be effectively controlled and industrial products and the raw materials thereof can be advantageously, protected from damages caused by various microorganisms.

The germicide according to the present invention can be used alone in the preparations thereof. It should be noted, however, that the active component of the present germicide can also be formulated into the preparations together with one or more agents such as various conventional insecticides, bactericides, fungicides, herbicides, plant growth regulators miticides, nematocides, attractants, repellents, nutrients, fertilizers, and soil structure conditioning agents. Thus, these preparations are expected to exhibit various wide effects.

The nonmedical fungicides can be used as a fungicide, in addition to the above-mentioned agricultural and garden fungicides, for preventing the industrial products and the raw materials thereof from adverse effects or damage caused by various microorganisms. Examples of such industrial products and the raw materials thereof are plastics, plasters, carpets, adhesives, emulsions (or emulsified liquids), paints, coating agents, hides, glues, wood (or timbers), fibers, paper, and cardboard. Further, the present fungicides can be similarly applied to the portions of industrial plants such as cooling water circulation system and cooling lubricating oil circulation system.

EXAMPLE

The present invention will be further explained by, but is by no means limited to, the following Synthetic Examples, Formulation Examples, and Test Examples. In Synthetic Examples, $^{19}$Fnmr and $^1$Hnmr are the NMR data determined by using trifluoro acetic acid as an outer standard and tetramethyl silane as an inner standard, respectively, unless otherwise specified.

SYNTHETIC EXAMPLE 1

Synthesis of 4-Amino-2,5,6-trifluoroisophthalonitrile (i.e., Compound No. 1)

To a solution of 2.0 g of tetrafluoroisophthalonitrile in 20 ml of acetonitrile, 0.6 ml of 28% aqueous ammonia was dropwise added. After the dropwise addition, the mixture was stirred at room temperature for one hour. An aqueous sodium bicarbonate solution was added to the mixture and the resultant mixture was extracted with chloroform and was washed with an aqueous sodium chloride solution. After drying with sodium sulfate, the chloroform was distilled off to obtain yellow crystal. The resultant crystal was recrystallized from chloroform to obtain 1.2 g (61% yield) of the desired compound No. 1.

The analytical results are as follows.

$^{19}$Fnmr (CCl$_4$/DMSOd$_6$) δ25.0 (d, J$_{FF}$=9.4 Hz, 1F) 46.7 (d, J$_{FF}$=18.8 Hz, 1F) 80.0 (dd, J$_{FF}$=18.8 Hz, 9.4 Hz, 1F).

$^1$Hnmr (CCl$_4$/DMSOd$_6$) δ2.8 (s).

SYNTHETIC EXAMPLE 2

Synthesis of 4-Anilino-2,4,6-trifluoroisophthalonitrile (i.e., Compound No. 6)

A solution of 0.85 g of aniline in 20 ml of acetonitrile was dropwise added, while stirring, to a solution of 2.0 g of tetrafluoroisophthalonitrile and 2.0 g of triethylamine in 30 ml of acetonitrile. After dropwise adding, the mixture was stirred at room temperature for 1 hour and an aqueous sodium bicarbonate solution was then added. The mixture was extracted with chloroform and the chloroform extract was washed 5 times with an aqueous sodium chloride solution. After drying with magnesium sulfate, the chloroform was distilled off. The resultant crude crystal was purified by silica gel chromatography (solvent:hexane). Thus, 2.3 g (87% yield) of the desired compound No. 6 was obtained.

The analytical results are as follows.

$^{19}$Fnmr (CCl$_4$/DMSOd$_6$) δ24.3 (d, J$_{FF}$=9.4 Hz, 1F); 45.4 (d, J$_{FF}$=19.0 Hz, 1F); 72.7 (dd, J$_{FF}$=19.0 Hz, 9.4 Hz, 1F).

$^1$Hnmr (CCl$_4$/DMSOd$_6$) δ3.7 (s, 1H), 7.4 (s, 5H).

SYNTHETIC EXAMPLE 3

Synthesis of 4-Diethylamino-2,5,6-trifluoroisophthalonitrile (i.e., Compound No. 14)

The desired compound was prepared in the same manner as in Synthetic Example 2 by using diethyl amine in lieu of the aniline. The resultant yellow liquid was distilled in vacuo to obtain 2.0 g (91% yield) of the desired compound No. 14 as a fraction at a boiling point of 144° C. to 146° C./7 mmHg.

The analytical results are as follows.

$^{19}$Fnmr (CCl$_4$/DMSO-d$_6$) δ23.4 (dd, J$_{FF}$=9 Hz, 1.8 Hz, 1F) 43.2 (dd, J$_{FF}$=18 Hz, 1.8 Hz, 1F) 69.5 (ddd, J$_{FF}$=18 Hz, 9 Hz, 1F).

$^1$Hnmr (CCl$_4$/DMSO-d$_6$) δ1.2 (t, 3H); 3.4 (q, 2H).

SYNTHETIC EXAMPLE 4

Synthesis of 2,4,5-Trifluoro-6-hydroxyisophthalonitrile (i.e., Compound No. 19)

A 2.0 g amount of tetrafluoroisophthalonitrile and 0.7 g of sodium hydroxide were added to 40 ml of water and the mixture was heated under reflux for 1.5 hours. After cooling, the mixture was neutralized with concentrated hydrochloric acid and was then extracted with ether. After the ether extract was washed with water, the extract was dried with magnesium sulfate. The solvent was distilled off and the resultant crude crystal was recrystallized to obtain 1.39 g of the desired compound No. 19.

The analytical results are as follows.

Elementary analysis C, Found 48.32%; Calc. 48.5%; H Found 0.51%; Calc. 0.55%; N Found 14.0%; Calc. 14.1%.

$^{19}$Fnmr (CCl$_4$/DMSOd$_4$) δ25.5 (d, J$_{FF}$=9.35 Hz, 1F); 43.0 (d, J$_{FF}$=19.6 Hz, 1F); 78.7 (dd, J$_{FF}$=9.35 Hz, J$_{FF}$=19.6 Hz, 1F).

$^1$Hnmr (CCl$_4$/DMSOd$_6$) δ2.50 (S, 1H)

SYNTHETIC EXAMPLE 5

Synthesis of 2,4,5-Trifluoro-6-methoxyisophthalonitrile (i.e., Compound No. 20)

A 2.0 g amount of tetrafluoroisophthalonitrile was heated under reflux in 40 ml of methanol for 4 hours. The methanol was distilled off in vacuo to approximately one-fifth volume and ice water was then poured to the resultant mixture. The precipitated crystal was collected by filtration and was then washed with water and a small amount of cold methanol. After drying in vacuo, 1.6 g of the desired compound No. 20 was obtained.

The analytical results are as follows.

$^{19}$Fnmr (CCl$_4$/DMSOd$_6$) δ24 (d, J$_{FF}$=13 Hz, 1F); 38 (d, J$_{FF}$=20 Hz, 1F); 75 (dd, J$_{FF}$=20 Hz, J$_{FF}$=13 Hz, 1F).

$^1$Hnmr (CCl$_4$/DMSOd$_6$) δ4.3 (S, 3H).

SYNTHETIC EXAMPLE 6

Synthesis of 4-Ethoxy-2,5,6-trifluoroisophthalonitrile (i.e., Compound No. 21)

The desired compound was obtained in the same manner as in Synthetic Example 5, except that ethanol was used in lieu of methanol. The yield was 90%.

The analytical results are as follows.

$^{19}$Fnmr (CCl$_4$/DMSOd$_6$) δ22.7 (d, J$_{FF}$=10.2 Hz, 1F); 32.7 (d, J$_{FF}$=18.7 Hz, 1F); 75.2 (dd, J$_{FF}$=18.7 Hz, J$_{FF}$=10.1 Hz, 1F).

$^1$Hnmr (CCl$_4$/DMSOd$_6$) δ1.5 (t, J$_{HH}$=8 Hz, 3H); 4.7 (q, J$_{HH}$=8 Hz, 2H).

SYNTHETIC EXAMPLE 7

Synthesis of 2,5,6-Trifluoro-4-isopropoxyisophthalonitrile (i.e., Compound No. 24)

The desired compound was obtained in the same manner as in Synthetic Example 5, except that isopropanol was used in lieu of methanol.

The yield was 86%.

SYNTHETIC EXAMPLE 8

Synthesis of 2,4,5-Trifluoro-6-phenoxyisophthalonitrile (i.e., Compound No. 29)

A mixture of 2.0 g of isotetrafluorophthalonitrile, 1.0 g of phenol, and 3 g of potassium fluoride was heated under reflux for 1.5 hours in 30 ml of acetonitrile. After adding 40 ml of water, the reaction mixture was extracted with chloroform. After washing with water, the extract was dried with magnesium sulfate and the solvent was then distilled off to obtain 2.6 g of the residue. The crude product thus obtained was treated by silica gel chromatography (solvent:chloroform) to obtain 1.7 g (64% yield) of the desired compound in the form of crystal.

The analytical results are as follows.

$^{19}$Fnmr (CDl$_4$/DMSOd$_6$) δ34.5 (d, J$_{FF}$=12 Hz, 1F); 57.0 (d, J$_{FF}$=18 Hz, 1F); 85.5 (dd, J$_{FF}$=18 Hz, J$_{FF}$=12 Hz, 1F).

$^1$Hnmr (CCl$_4$/DMSOd$_6$) δ7-8 (m).

SYNTHETIC EXAMPLE 9

Synthesis of 2,4,5-trifluoro-6-(2,6-xylyloxy)isophthalonitrile (i.e., Compound No. 37)

A solution of 1.2 g ($10 \times 10^{-3}$ mol) of 2,6-dimethylphenol in 40 ml of acetonitrile was dropwise added at a temperature of $-10°$ C. to a solution of 2.0 g ($10 \times 10^{-3}$ mol) of tetrafluoroisophthalonitrile and 2.9 g ($50 \times 10^{-3}$ mol) of potassium fluoride. The mixture was allowed to stand at a temperature of $-10°$ C. to $0°$ C. for 1 hour while stirring and the undissolved potassium fluoride was separated by filtration. The filtrate was concentrated to dryness in vacuo. The resultant residue was dissolved in a mixed solvent of acetone and cyclohexane and 2.3 g (77% yield) of the desired compound No. 37 was obtained as white crystal.

The analytical results are as follows.

$^{19}$F-NMR (acetone) $\delta 26.0$ (d, $J_{FF}=8.7$ Hz, 1F); 41.0 (d, $J_{FF}=16.4$ Hz, 1F); 80.0 (dd, $J_{FF}=8.7$, 16.4 Hz, 1F).

$^1$H-NMR (CDCl$_3$) $\delta 2.15$ (S, 6H); 6.95–7.1 (m, 3H).

SYNTHETIC EXAMPLE 10

Synthesis of 2,4,5-Trifluoro-6-phenylthioisophthalonitrile (i.e., Compound No. 41)

A 2.0 g amount of tetrafluoroisophthalonitrile and 0.87 g of potassium fluoride were dissolved in 10 ml of acetonitrile. After cooling the mixture to a temperature of $0°$ C. by an ice-water bath, 1.1 g of phenyl mercaptan was dropwise added by a syringe. While mixture was maintained at a temperature of about $0°$ C., the mixture was stirred for 8 hours and the solvent was then distilled off. A 50 ml amount of water was added to the mixture and potassium fluoride was dissolved. The mixture was extracted with chloroform, and the extract was dried with magnesium sulfate. The chloroform was distilled off in vacuo and the resultant liquid was then distilled in vacuo to obtain 1.8 g (63% yield) of the desired compound No. 41 at a boiling point of $65°$ C. to $67°$ C./0.7 mmHg.

The analytical results are as follows.

$^{19}$Fnmr (CCl$_4$/DMSOd$_6$) $\delta 23.1$ (d, $J_{FF}=11.9$ Hz, 1F); 38.2 (d, $J_{FF}=18.9$ Hz, 1F); 49.4(dd, $J_{FF}=18.9$ Hz, 11.9 Hz, 1F).

$^1$Hnmr (CCl$_4$/DMSOd$_6$) $\delta 7.4$ (S).

SYNTHETIC EXAMPLE 11

Synthesis of 2,4,5-Trifluoro-6-methallyloxyisopthalonitrile (i.e., Compound No. 42)

The mixture of 3.0 g of tetrafluoroisophthalonitrile, 1.2 g of $\beta$-methallyl alcohol and 1.8 g of potassium fluoride in 30 ml of acetonitrile was stirred at room temperature for 10 hours. The mixture was cooled and filtered. The filtrate was evaporated under reduced pressure. After 50 ml of water was added to the residue, the mixture was extracted with carbon tetrachloride, washed with water, and dried over sodium sulfate. After evaporating carbon tetrachloride, the residue of 2.9 g (crystal) was obtained.

The analytical results are as follows.

mp<$50°$ C.

$^1$Hnmr (CDCl$_3$) $\delta 1.88$ (3H, s), $\delta 4.9–5.2$ (H, m).

SYNTHETIC EXAMPLE 12

Synthesis of 4-Allyloxy-2,5,6-trifluoroisophthalonitrile (i.e., Compound No. 27)

The desired compound was obtained in the same manner as in Synthetic Example 11, except that allyl alcohol was used in lieu of methallyl alcohol.

The analytical results are as follows.

$^{19}$Fnmr (CCl$_4$/DMSOd$_6$) $\delta 25.5$ (d, $J_{FF}=9.0$ Hz, 1F); 39.8 (d, $J_{FF}=18.4$ Hz, 1F); 75.3 (m, 1F).

SYNTHETIC EXAMPLE 13

Synthesis of 2,4,5-Trifluoro-6-(2-methoxyethoxy)isophthalonitrile (i.e., Compound No. 43)

The mixture of 3.0 g tetrafluoroisophthalonitrile, 1.2 g of methyl cellosolve, and 1.8 g of potassium fluoride in 30 ml of acetonitrile was stirred at room temperature for 8 hours. The mixture was filtered. The filtrate was evaporated under reduced pressure. After 50 ml of water was added to the residue, the mixture was extracted with dichloromethane, washed with water, and dried over sodium sulfate. After evaporating dichloromethane, residue of 3.4 g was obtained. By column chromatography (Wakogel C-200; solvent-CH$_2$Cl$_2$) pure oil (3.0 g) was isolated.

$^1$Hnmr (CDCl$_3$) 3.38 (3H, s), 3.83 (2H, t, J=6 Hz), 4.63 (2H, m).

SYNTHETIC EXAMPLE 14

Synthesis of 2,4,5-Trifluoro-6-tetrahydrofurfuryloxyisophthalonitrile (i.e., Compound No. 44)

The mixture of 3.0 g of tetrafluoroisophthalonitrile, 1.7 g of furfuryl alcohol, and 1.8 g of potassium fluoride in 30 ml of acetonitrile was stirred at room temperature for 10 hours. The mixture was filtered. The filtrate was evaporated under reduced pressure. After 50 ml of water was added to the residue, the mixture was extracted with chloroform, washed with water and dried over magnesium sulfate. After evaporating chloroform, residue of 3.8 g was obtained. By column chromatography (florisil; solvent-chloroform) pure oil (3.2 g) was isolated.

SYNTHETIC EXAMPLE 15

Synthesis of 2,4,5-Trifluoro-6-cyclohexanyloxyisophthalonitrile (i.e., Compound No. 46)

A 5.0 g amount of tetrafluoroisophthalonitrile and 2.18 g of potassium fluoride were dissolved in 25 ml of acetonitrile, and 3.83 g of cyclohexanol was then dropwise added to the mixture. After the dropwise addition, the mixture was stirred at room temperature for 24 hours. The reaction mixture was filtered, the filtrate was concentrated in vacuo, and the concentrated liquid was poured to 50 ml of water. The resultant mixture was extracted with carbon tetrachloride. After washing with water, the extract was dried with anhydrous magnesium sulfate and the solvent was then distilled off. Thus, 6.2 g (88% yield) of the desired compound No. 47 was obtained.

The analytical results are as follows.

$^{19}$Fnmr (CDCl$_3$).

$\delta$: 26.0 (d, $J_{FF}=9.4$ Hz, 1F); 41.0 (d, $J_{FF}=16.9$ Hz, 1F); 75.5 (ddt, $J_{FF}=9.4$ Hz, $J_{FF}=16.9$ Hz, 1F).

SYNTHETIC EXAMPLE 16

Synthesis of 2,4,5-Trifluoro-6-sec-butoxyisophthalonitrile (i.e., Compound No. 48)

A 3.0 g amount of tetrafluoroisophthalonitrile and 1.26 g of 20 ml acetonitrile were dissolved in 20 ml of acetonitrile. A 1.66 g amount of sec-butanol was dropwise added to the mixture and the mixture was then stirred at room temperature for 24 hours. After the mixture was filtered, the filtrate was concentrated in vacuo and the concentrated liquid was poured into 50 ml of water. The mixture was extracted with carbon tetrachloride. After washing with water, the resultant mixture was dried with anhydrous magnesium sulfate and the solvent was then distilled off. Thus, 3.4 g (89% yield) of the desired compound No. 48 was obtained.

The analytical results are as follows.

$^{19}$Fnmr (CDCl$_3$).

δ: 23.7 (d, $J_{FF}$=9.6 Hz, 1F); 38.7 (d, $J_{FF}$=16.9 Hz, 1F); 74.3 (dd, $J_{FF}$=16.9 Hz, $J_{FF}$=9.6 Hz, 1F).

IR (KB$_r$)

2250 cm$^{-1}$ (C≡N).

SYNTHETIC EXAMPLE 17

Synthesis of 2,4,5-Trifluoro-6-propylthioisophthalonitrile (i.e., Compound No. 50)

A 2.0 g amount of tetrafluoroisophthalonitrile and 0.87 g of potassium fluoride were dissolved in 10 ml of acetonitrile. After cooling the mixture to a temperature of 0° C., 0.76 g of n-propylmercaptan was gradually dropwise added to the mixture and the resultant mixture was stirred at a temperature of 0° C. or less for 12 hours. To the reaction mixture, 50 ml of water was added. The mixture was then extracted with chloroform. After washing with a saturated aqueous sodium bicarbonate solution, the mixture was dried with anhydrous magnesium sulfate. The chloroform was distilled off and the crude product was treated by silica gel column chromatography (solvent:n-hexane/ethyl acetate=3/1).

Thus, 1.7 g (66% yield) of the desired compound No. 52 was obtained. The analytical results are as follows.

$^{19}$Fnmr (CCl$_4$).

δ: 22.0 (d, $J_{FF}$=13.2 Hz, 1F); 38.7 (d, $J_{FF}$=20.7 Hz, 1F); 51.7 (ddt, $J_{FF}$=13.2 Hz, $J_{FF}$=20.7 Hz, 1F).

SYNTHETIC EXAMPLE 18

Synthesis of 2,4,5-trifluoro-6-isopropylthioisophthalonitrile (i.e., Compound No. 51)

The desired compound was prepared in the same manner as in Synthetic Example 17, except that the isopropylmercaptan was used in lieu of n-propylmercaptan. Thus, 1.6 g (63% yield) of the desired compound No. 51 was obtained.

The analytical results are as follows.

$^{19}$Fnmr (CCl$_4$).

δ: 22.3 (d, $J_{FF}$=13.0 Hz, 1F); 38.3 (d, $J_{FF}$=20.2 Hz, 1F); 50.5 (ddt, $J_{FF}$=13.0 Hz, $J_{FF}$=20.2 Hz, 1F).

SYNTHETIC EXAMPLE 19

Synthesis of 2,4,5-Trifluoro-6-n-butylthioisophthalonitrile (i.e., Compound No. 52)

A 2.0 g amount of tetrafluoroisophthalonitrile and 0.87 g of potassium fluoride were dissolved in 10 ml of acetonitrile. After cooling to a temperature of 0° C., 0.90 g (1.04 ml) of n-butylmercaptan was gradually dropwise added to the mixture and the resultant mixture was stirred at a temperature of 0° C. or less for 12 hours. After 50 ml of water was added to the reaction mixture, the reaction mixture was extracted with chloroform and the extract was then washed with a saturated aqueous sodium bicarbonate solution, followed by drying with anhydrous magnesium sulfate. After distilling off the chloroform, the resultant crude product was distilled in vacuo. Thus, 2.08 g (77% yield) of the desired compound No. 52 was obtained.

The analytical results are as follows.

$^{19}$Fnmr (CCl$_4$).

δ: 23.3 (d, $J_{FF}$=14.1 Hz, 1F); 39.2 (d, $J_{FF}$=21.4 Hz, 1F); 52.3 (ddt, $J_{FF}$=14.1 Hz, $J_{FF}$=21.4 Hz, 1F).

SYNTHETIC EXAMPLE 20

Synthesis of 2,4,5-Trifluoro-6-isobutylthioisophthalonitrile (i.e., Compound No. 53)

The desired compound was obtained in the same manner as in Synthetic Example 19, except that isobutylmercaptan was used in lieu of n-butylmercaptan.

Thus, 2.02 g (75% yield) of the desired compound was obtained.

The analytical results are as follows.

$^{19}$Fnmr (CCl$_4$).

δ: 22.0 (d, $J_{FF}$=11.3 Hz, 1F); 38.3 (d, $J_{FF}$=18.8 Hz, 1F); 51.5 (ddt, H$_{FF}$=11.3 Hz, $J_{FF}$=18.8 Hz, 1F).

FORMULATION EXAMPLE 1

Powder germicides having the following compositions were prepared by mixing the ingredients listed below at room temperature.

| Ingredient | Parts by weight |
| --- | --- |
| Compound listed in Table 1 | 3 |
| Clay | 40 |
| Talc | 57 |

The powder germicides thus obtained were evaluated in the Test Examples below.

FORMULATION EXAMPLE 2

Wettable powder germicides having the following compositions were prepared by mixing the ingredients listed below at room temperature.

| Ingredient | Parts by weight |
| --- | --- |
| Compound listed in Table 1 | 75 |
| Polyoxyethyiele alkylallylether | 9 |
| White carbon | 16 |

The wettable powder germicides thus obtained were evaluated in the Test Examples below.

TEST EXAMPLE 1

Evaluation test of antibacterial and antifungal activity against pathogenic bacteria and fungi of plant Conidia of pathogenic fungi and bacteria of plants cultivated on culture media were uniformly mixed in a PSA culture medium and a constant amount of the resultant mixture was poured into a vessel. Thus, uniform plates were prepared.

After solidifying, a filter paper having a diameter of 8 mm, which was prepared by absorbing a certain amount of the active compound, followed by air drying, was placed on the plate. After 48 hour incubation, the diameter of the inhibited circle was measured. Two tests were carried out in each run.

The results are shown in Table 2.

TABLE 2

| Compound No. | Concentration (a.i. ppm) | Diameter (mm) of Inhibited Circle | | | |
|---|---|---|---|---|---|
| | | B.c*[1] | A.k*[1] | P.o*[1] | X.c*[1] |
| 1 | 500 | 0 | 0 | 30.5 | 16.8 |
| 2 | " | 0 | 0 | 14.3 | 15.0 |
| 3 | " | 0 | 0 | 14.0 | 22.5 |
| 4 | " | 0 | 17.3 | 19.8 | 20.0 |
| 5 | " | 0 | 0 | 15.5 | 13.3 |
| 6 | " | 0 | 0 | 22.5 | 13.8 |
| 7 | " | 0 | 0 | 10.2 | 0 |
| 8 | " | 0 | 0 | 15.5 | 0 |
| 9 | " | 31.5 | 0 | 30.8 | 0 |
| 10 | " | 0 | 0 | 10.2 | 0 |
| 11 | " | 31.0 | 0 | 18.5 | 30.0 |
| 12 | " | 30.8 | 14.5 | 34.3 | 0 |
| 13 | " | 0 | 0 | 10.2 | 0 |
| 14 | " | 22.5 | 22.5 | 34.3 | 0 |
| 15 | " | 0 | 0 | 13.3 | 0 |
| 16 | " | 0 | 0 | 11.5 | 0 |
| 17 | " | 0 | 10.2 | 10.2 | 0 |
| 18 | " | 0 | 0 | 10.2 | 0 |
| 19 | 11 | 31.2 | 0 | 33.7 | 0 |
| 20 | 500 | 38.9 | 29.0 | 35.2 | 28.0 |
| 21 | " | 33.0 | 13.4 | 19.8 | 30.5 |
| 22 | " | 30.2 | 31.5 | 21.5 | 16.4 |
| 23 | " | 31.5 | 32.3 | 30.2 | 30.4 |
| 24 | " | 33.5 | 33.5 | 34.1 | 30.5 |
| 25 | " | 32.1 | 31.5 | 33.0 | 31.5 |
| 26 | " | 15.0 | 30.5 | 29.0 | 28.0 |
| 27 | " | 30 | 30 | 34.8 | 28.8 |
| 28 | " | 22.5 | 29.0 | 30.5 | 28.2 |
| 29 | " | 29.8 | 30.5 | 33.0 | 0 |
| 30 | " | 17.0 | 12.5 | 12.3 | 0 |
| 31 | " | 30.3 | 17.7 | 24.5 | 10.0 |
| 32 | " | 18.0 | 12.5 | 13.8 | 11.0 |
| 33 | " | 20.0 | 13.8 | 15.0 | 12.3 |
| 34 | " | 20.5 | 15.0 | 15.5 | 11.8 |
| 35 | " | 20.0 | 19.2 | 15.5 | 12.5 |
| 36 | " | 18.0 | 16.0 | 16.0 | 0 |
| 37 | " | 13.5 | 0 | 13.5 | 10.0 |
| 38 | " | 22.5 | 13.2 | 14.0 | 0 |
| 39 | " | 19.8 | 12.5 | 12.2 | 0 |
| 40 | " | 21.3 | 13.8 | 15.3 | 0 |
| 42 | " | 30.0 | 33.5 | 34.1 | 29.2 |
| 43 | " | 28.5 | 30.8 | 32.8 | 22.5 |
| 44 | " | 27.8 | 29.2 | 30.5 | 19.8 |
| 45 | " | 19.8 | 22.5 | 21.5 | 28.0 |
| 46 | " | 13.5 | 15.8 | 18.3 | 0 |
| 47 | " | 31.0 | 33.2 | 32.5 | 29.0 |
| 48 | " | 14.8 | 30.0 | 28.0 | 27.5 |
| 49 | " | 30.2 | 15.5 | 31.5 | 10.0 |
| 50 | " | 30.0 | 30.5 | 28.2 | 29.8 |
| 51 | " | 32.2 | 31.0 | 32.5 | 28.8 |
| 52 | " | 30.0 | 29.8 | 30.5 | 28.0 |
| 53 | " | 15.0 | 28.2 | 27.0 | 26.0 |
| 54 | " | 15.0 | 28.8 | 28.0 | 26.8 |
| Daconil*[2] | " | 16.1 | 15.4 | 15.5 | — |

*[1]B.c: Gray mold of vegetables
A.k: Black spot of pear
P.o: Blast of rice
X.c: Canker of citrus fruit
*[2]Comparative test, available from SDS Biotech K.K.

TEST EXAMPLE 2

Evaluation test of antifungal activity against black spot of pear

A sample agent diluted to a certain concentration was uniformly sprayed on the developed leaves of pear trees (variety: Nijyusseiki) in an amount of 20 ml per 5 leaves and was dried in a room.

After air drying, conida of *Alternaria kikuchiana* formed on an apricot culture medium were sprayed on and was inoculated on the leaves. The incubation was carried out at a temperature of 25° C. and a relative humidity of 100% for 3 days. After 3 days, the infected area was measured. Five tests were carried out in each run.

The results are shown in Table 3.

TABLE 3

| Compound No. | Concentration (a.i. ppm) | Average infected area (%) | Controlled value (%) |
|---|---|---|---|
| 1 | 500 | 0.3 | 99.7 |
| 2 | " | 0 | 100 |
| 3 | " | 5.3 | 94.7 |
| 6 | " | 0 | 100 |
| 7 | " | 10.0 | 90.0 |
| 12 | " | 5.6 | 94.4 |
| 20 | " | 15.0 | 85.0 |
| 23 | " | 5.1 | 94.9 |
| 24 | " | 3.2 | 96.8 |
| 25 | " | 41.0 | 59.0 |
| 26 | " | 65.0 | 35.0 |
| 28 | " | 28.5 | 71.5 |
| Rovral*[1] | " | 5.2 | 94.8 |
| Control*[2] | — | 100 | — |

*[1]Comparative test, available from RHONE POULENC
*[2]No treatment

TEST EXAMPLE 3

Evaluation test of antifungal effect against rice blast disease

A sample liquid agent containing a certain amount of an active compound was uniformly sprayed on rice seedlings (variety: Jyukkoku) at true leaf stage in a pot with the volume of 200 liter/10 a and was air-dried in a green house.

After air drying, a spore suspension previously prepared in such a way that 40 conidia of rice blast fungus were present in a visual area of a 100 magnification microscope was uniformly sprayed and inoculated. Immediately, the sprayed rice seedlings were allowed to stand under dark conditions of a temperature of 23° C. and a relative humidity of 100%. After 48 hours, the rice seedlings were transferred to a green house and, after 10 days from the inocuration, the degree of the infection was determined. The inhibition value was calculated as follows. Three tests were carried out in each run.

$$\text{Degree of infection} = \frac{\Sigma nf}{4N}$$

wherein
n: Number of leaves in each infection degree
f: index of refraction degree
N: Number of leaves examined

| Index of infection degree | Number of lesion per leaf |
|---|---|
| 0 | 0 |
| 1 | 1–3 |
| 2 | 4–6 |
| 3 | 7–10 |
| 4 | 11 or more |

The results are as shown in Table 4.

TABLE 4

| Compound No. | Concentration (a.i. ppm) | No. of leaves examined | No. of leaves in each infection degree | | | | | % of infected leaves | Infection degree | Chemical injury |
|---|---|---|---|---|---|---|---|---|---|---|
| | | | 0 | 1 | 2 | 3 | 4 | | | |
| 38 | 500 | 185 | 163 | 19 | 3 | 0 | 0 | 13.5 | 3.4 | — |
| Fujione*[1] | 500 | 180 | 152 | 22 | 6 | 0 | 0 | 15.6 | 4.7 | — |
| Control*[2] | — | 184 | 0 | 50 | 85 | 40 | 9 | 100 | 51.1 | — |

*[1]Comparative test, commercially available from NIPPON NOHYAKU K.K.
*[2]No treatment

TEST EXAMPLE 4

Evaluation test of antifungal effect against rice blast disease

Test Example 3 was repeated except that the active compound was changed.

The results are as shown in Table 5.

TABLE 5

| Compound No. | Concentration (a.i. ppm) | No. of leaves examined | No. of leaves in each infection degree | | | | | % of infected leaves | Infection degree | Chemical injury |
|---|---|---|---|---|---|---|---|---|---|---|
| | | | 0 | 1 | 2 | 3 | 4 | | | |
| 44 | 500 | 249 | 168 | 57 | 24 | 0 | 0 | 32.5 | 10.5 | — |
| Fujione*[1] | 500 | 280 | 190 | 70 | 10 | 10 | 0 | 32.1 | 10.7 | — |
| Control*[2] | — | 270 | 20 | 110 | 90 | 40 | 10 | 92.6 | 41.7 | — |

*[1]Comparative test, commercially available from NIPPON NOHYAKU K.K.
*[2]No treatment

TEST EXAMPLE 5

Antifungal spectrum test against spores by agar dilution streak method

A 10 ml amount of a potato-agar medium containing a certain concentration of each active ingredient was poured into a petri dish. After solidifying, a spore suspension of each test microorganism having 2.00 to $3.00 \times 10^6$ spores/ml was inoculated in the form of streaks with a platinum loop amount. The petri dish was allowed to stand in a constant temperature room at 25° C. for 3 days. Thereafter, the degree of growth was examined and the minimum inhibition concentration (i.e., "MIC") was determined. Four tests were carried out in each run.

The results are as shown in Table 6.

TABLE 6

| Compound No. | MIC (ppm) Microorganism*[1] | | | | |
|---|---|---|---|---|---|
| | A | B | C | D | E |
| 14 | <5 | <5 | 50 | 50 | >50 |
| 20 | <5 | <5 | <5 | 5 | 10 |
| 21 | <5 | <5 | <5 | 10 | 25 |
| 22 | <5 | <5 | <5 | <5 | >50 |
| 23 | <5 | <5 | <5 | 10 | 50 |
| 24 | <5 | <5 | <5 | 10 | 25 |
| 25 | <5 | <5 | <5 | 10 | 25 |
| 26 | <5 | <5 | 10 | 25 | 50 |
| 27 | <5 | <5 | 5 | 5 | 10 |
| 28 | <5 | <5 | 10 | 10 | 25 |
| 31 | <5 | <5 | <5 | 10 | >50 |
| 42 | <5 | <5 | 5 | 10 | 20 |
| 43 | <5 | <5 | 10 | 20 | 20 |
| 44 | 5 | 10 | 20 | 20 | 20 |
| 47 | <5 | <5 | 5 | 10 | 10 |
| 48 | <5 | <5 | 5 | 10 | 10 |
| 50 | <5 | <5 | 10 | 10 | 20 |
| 51 | <5 | <5 | 10 | 20 | 10 |
| 53 | <5 | <5 | 20 | 20 | 20 |
| 54 | <5 | 5 | 20 | 20 | 20 |
| Daconil*[2] | <5 | 50 | 10 | 5 | >50 |

*[1]A: *Penicillium funiculosum*
B: *Aspergillus niger*
C: *Fusarium proliferatum*
D: *Gliocladium virens*
E: *Rhizopus storonifer*
*[2]Comparative test, available from SDS Biotech K.K.

TEST EXAMPLE 6

Antifungal spectrum test against conidium by agar dilution method

A 10 ml amount of a potato-agar medium containing a certain concentration of each active ingredient was poured into a petri dish. After solidifying, the tip portion of the flora of each test microorganism previously incubated on a plate culture medium, which was punched with a 8 cm$\phi$ cork borer, was inoculated in the active ingredient containing culture medium. The culture medium thus obtained was allowed to stand in a constant temperature room at 28° C. for 3 days. Therefore, the growth of the microorganism was examined and the MIC was determined. Four tests were carried out in each run.

The results are as shown in Table 7.

TABLE 7

| Compound | MIC (ppm) Microorganism*[1] | | | | |
|---|---|---|---|---|---|
| | A | B | C | D | E |
| 14 | 10 | 10 | <50 | 10 | 10 |
| 20 | 5 | 5 | 10 | 10 | 10 |
| 21 | 5 | 10 | 10 | 10 | 10 |
| 22 | 25 | 25 | 25 | 10 | 25 |
| 23 | 5 | 10 | 10 | 10 | <5 |
| 24 | 10 | 10 | 10 | 10 | 10 |
| 25 | 10 | 25 | 10 | 5 | 10 |
| 26 | 10 | 25 | 10 | <5 | <5 |
| 27 | 20 | 10 | 20 | 5 | 20 |
| 28 | 10 | 25 | 25 | 10 | <5 |
| 31 | 10 | 50 | 25 | 25 | 25 |
| 42 | 20 | 20 | 10 | 10 | 10 |
| 43 | 20 | 100 | 50 | 20 | 10 |
| 44 | 20 | 20 | 50 | 20 | 20 |
| 47 | 20 | 20 | 50 | 10 | 10 |
| 48 | 20 | 10 | 20 | 5 | 10 |

TABLE 7-continued

| Compound | MIC (ppm) Microorganism[1] | | | | |
|---|---|---|---|---|---|
| | A | B | C | D | E |
| 50 | 20 | 20 | 20 | 20 | 20 |
| 51 | 20 | 50 | 20 | 10 | 20 |
| 53 | 20 | 50 | 50 | 20 | 20 |
| 54 | 20 | 50 | 50 | 20 | 50 |
| Daconil*[1] | 50 | >50 | 50 | 50 | >50 |

*[1]See Remarks of Table 6

TEST EXAMPLE 7

Antibacterial spectrum test against bacteria by agar dilution streak method

A 10 ml amount of a normal bouillon-agar culture medium was poured into a petri dish. After solidifying, a bacterial suspension previously obtained from the cultivation in the same liquid medium was inoculated in the form of streaks with a platinum loop amount. The petri dish was allowed to stand for 2 days in a constant temperature room at 30° C. Thereafter, the growth of the microorganism was examined and the MIC was determined. Four tests were carried out in each run.

The results are as shown in Table 8.

TABLE 8

| Microorganism[1] | MIC (ppm) | | | |
|---|---|---|---|---|
| | F | G | H | I |
| Compound No. 14 | <5 | 10 | 50 | >50 |
| Daconil*[2] | <5 | 10 | >50 | >50 |

*[1]F: Bacillus subtilia
G: Staphylococcus aureus
H: Esherichia coli
I: Pseudomonas fluorescens
*[2]Commercially available from SDS Biotech K.K.

TEST EXAMPLE 8

For evaluation test of antibacterial action against bacterial soft rot disease of Japanese raddish the rhizome portion of Japanese raddish was cut to the form of a ring having a thickness of 1 cm with a 18 cm$\phi$ cork borer to form raddish chips. The chips were dipped in a liquid containing a certain concentration of an active ingredient for one hour. After air drying, one drop of a culture liquid containing bacterial soft rot bacteria which was cultivated at 27° C. for 24 hours in a normal bouillon medium by shaking culture, was inoculated in the center of the raddish chip. The raddish chip was allowed to stand at a temperature of 27° C. for 2 days under a high humidity condition. Therefore, the putrefaction degree of the raddish chip was examined. Five tests were carried out in each run.

The results are as shown in Table 9.

TABLE 9

| Compound No. | Concentration (a.i., ppm) | Degree of putrefaction*[3] |
|---|---|---|
| 27 | 500 | 0 |
| 42 | 500 | 1 |
| 43 | 500 | 0 |
| 44 | 500 | 0 |
| 45 | 500 | 3 |
| 46 | 500 | 4 |
| Copper hydroxide | 520 (as Cu) | 2 |
| Streptomycin | 200 | 0 |

*[1]Commercially available from Sankyoh K.K.

*[2]Commercially available from Meiji Seika K.K.

| *[3]Degree of Putrefaction | Putrefaction (%) |
|---|---|
| 0 | 0 |
| 1 | 1-10 |
| 2 | 11-25 |
| 3 | 26-50 |
| 4 | 51-75 |
| 5 | 76-100 |

We claim:

1. A fluorinated isophthalonitrile compound having the general formula

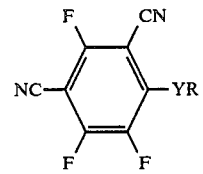

wherein Y is —O, —S, or —N(R'), R and R' are independently hydrogen, an alkyl group, an alkenyl group, an alkynyl group, a haloalkyl group, an alkoxyl group, an alkoxyalkyl group, a phenyl group which may be substituted, a tetrahydrofurfuryl group, or a cycloalkyl group, provided that, in the case of Y=—N(R'), R and R' or Y may be a heterocyclic compound residue.

2. A fluorinated isophthalonitrile compound as claimed in claim 1, wherein said compound is 2,4,5-trifluoro-6-methylamino-isophthalonitrile, 4-ethylamino-2,5,6-trifluoroisophthalonitrile, 4-diethylamino-2,5,6-trifluoroisophthalonitrile, 2,4,5-trifluoro-6-methoxyisophthalonitrile, 4-ethoxy-2,5,6-trifluoroisophthalonitrile, 2,4,5-trifluoro-6-propoxyisophthalonitrile, 2,4,5-trifluoro-6-isopoxyisophthalonitrile, 4-butoxy-2,5,6-trifluoroisophthalonitrile, 2,4,5-trifluoro-6-isobutoxyisophthalonitrile, 4-allyloxy-2,5,6-trifluoroisophthalonitrile, 2,4,5-trifluoro-6-methallyloxy-isophthalonitrile, 2,4,5-trifluoro-6-(2-methoxyethoxy)isophthalonitrile, 2,4,5-trifluoro-6-methylthioisophthalonitrile, 4-ethylthio-2,5,6-trifluoroisophthalonitrile, 2,4,5-trifluoro-6-propylthioisophthalonitrile, 2,4,5-trifluoro-6-isopropylthioisophthalonitrile, 4-butylthio-2,5,6-trifluoroisophthalonitrile, 2,4,5-trifluoro-6-isobutylthioisophthalonitrile, or 2,4,5-trifluoro-6-sec-butylthioisophthalonitrile.

3. A nonmedial fungicide comprising, as an effective ingredient, a fluorinated isophthalonitrile having the general formula

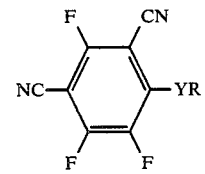

wherein Y is —O, —S, or —N(R'), R and R' and independently hydrogen, an alkyl group, an alkenyl group, an alkynyl group, a haloalkyl group, an alkoxyl group, alkoxyalkyl group, a phenyl group which may be substituted, a tetrahydrofurfuryl group, or a cycloalkyl group, provided that, in the case of Y=—N(R'), R and R' or Y may be a heterocyclic compound residue.

4. A nonmedical fungicide as claimed in claim 3, wherein said fungicide contains 1% to 95% by weight of the fluorinate isophthalonitrile.

* * * * *